United States Patent [19]

Jeffers et al.

[11] Patent Number: 5,264,833
[45] Date of Patent: Nov. 23, 1993

[54] AUTOMATIC LEAK DETECTOR

[76] Inventors: Edward Jeffers; Jose L. Sacerio, both of 1010 E. 31st St., Hialeah, Fla. 33013

[21] Appl. No.: 723,463
[22] Filed: Jun. 28, 1991
[51] Int. Cl.⁵ .......................................... G08B 17/10
[52] U.S. Cl. ................................ 340/632; 324/455; 324/464; 73/23.21; 73/40; 340/605
[58] Field of Search ............... 340/632, 939, 633, 634, 340/605; 324/464, 455, 468; 73/40.7, 31.03, 23.21, 40

[56] References Cited

U.S. PATENT DOCUMENTS 4,488,118 12/1984 Jeffers et al. ................ 340/632 X
4,831,332 5/1989 Rudisill et al. ............... 324/464 X
5,028,921 7/1991 Potter ............................ 340/939

*Primary Examiner*—Jeffrey Hofsass
*Attorney, Agent, or Firm*—Malin, Haley, DiMaggio & Crosby

[57] ABSTRACT

A method and apparatus are provided for automatically compensating for gain variations, component aging and drift characteristics of an associated circuit when trying to detect a leak. In the preferred embodiment an analog to digital converter will convert an analog signal from a sensor to a digital representation. A microprocessor will read the digital representation and compute the percentage change of the difference in values of the digital representations. Wherever the percentage change is greater than a threshold value, the microprocessor will activate an alarm to inform the user.

14 Claims, 3 Drawing Sheets

AUTOMATIC LEAK DETECTOR

BACKGROUND OF THE INVENTION

1. Field of the Invention

This invention relates generally to leak detectors and more particularly to a leak detector that automatically compensates for gain variations, component aging, drift characteristics of associated circuits as well as other non-desirable variables without requiring operator intervention.

2. Description of the Prior Art

One of the most common methods used to detect refrigerant gas leaks is by producing an electrical discharge or corona between two electrodes and sensing the change in corona current when refrigerant gas is present. There are many problems or variables which must be considered when designing a practical corona discharge detector. Some of these apply only to the corona gap sensor itself while others apply to both the sensor and the associated circuitry used to detect the current changes and produce an output. The following is an outline of some of the factors which must be considered when designing such an instrument.

I. Modes of "Drift" in Corona Sensor and High Voltage Supply
1. Temperature
2. Humidity
3. Aging
4. Power supply changes due to temperature effects and in battery-powered units, the battery condition II. Other "Variables" in Corona Sensor
1. Mechanical Construction
2. Materials III. Modes of "Drift" in Detecting an Alarm Circuit
1. Temperature effects of components and thresholds
2. Leakage paths IV. Other "Variables" in Detecting an Alarm Circuit
1. Component Tolerances
2. Variations in threshold values of active components
3. Variations in gain of active components Many methods have been proposed to compensate for some of these variables in a sensor for detecting refrigerant gas, which are very similar to and are present in almost all types of sensors to some degree. The following is a list of known patents which describe various means of adjusting and/or compensating for some of these variables:

Lieberman U.S. Pat. No. 4,282,521;
Roberts U.S. Pat. No. 3,076,139;
Jeffers, Sacerio U.S. Pat. No. 4,488,118;

Lieberman U.S. Pat. No. 4,282,521 is described as a method and apparatus for automatically recalibrating a leak detector. However, this circuit is nothing more than a circuit designed to balance at the level seen by the sensor at the time the operator turns the unit on. The circuit does this by storing a charge on a capacitor representative of the signal at turn-on, and subsequently sounding an alarm only if the signal at the input exceeds that stored value. It does nothing automatically and requires operator intervention to re-initiate the balance cycle. Theoretically, by turning the circuit on one in a contaminated area, the circuit will respond only to a higher concentration than that seen at turn on.

Another method commonly used to adjust the sensitivity is by adjusting a potentiometer. This method has the advantage over the Lieberman patent by knowing approximately how much you are desensitizing the unit and enables you to tune out only that portion that you desire. However, this manual method is time-consuming and requires some degree of operator skill.

Another technique is to compacitively couple the sensor signal to an alarm circuit which is designed to give a broad response versus freon concentration eliminating the need to bias out unwanted signals or re-adjust the sensitivity at all. However, since the alarm circuit is always active, it can be annoying to the operator when heavy contamination exists.

Another method is described in Jeffers, Sacerio U.S. Pat. No. 4,488,118 which adjusts the corona voltage to produce a predetermined corona current regardless of the background contamination level. However, this method also requires operator intervention to reset or rebalance the instrument. In addition, U.S. Pat. No. 4,831,332 describes a gas leak detector.

Therefore, a need exists for a leak detector which overcomes all of the disadvantages of the prior art including operator intervention, gain variations, component sensitivities and drift characteristics of components.

SUMMARY OF THE INVENTION

It is an object of the invention to automatically provide a calibrated output from a device that is independent of the sensitivity of the sensor by measuring the percentage change of the sensor output as opposed to measuring the absolute change.

It is another object of the invention to automatically adjust the gain of an indicated circuit to accommodate, without saturation, changes in the full scale value of the input signal.

It is yet another object of the invention to automatically compensate for drift due to sensor aging and temperature variations.

It is still another object of the invention to enable a device to provide a calibrated output independent of the sensitivity of a sensor connected to the device.

It is even still another object of the invention to automatically reference the output of a sensor to obtain a zero baseline reference and to automatically adjust the threshold of the output indicating circuit proportionally thereto. These and other objects of the invention will be accomplished by an apparatus which consists of an analog to digital converter which converts the output of the sensor to a digital signal which is then read by a microprocessor.

The microprocessor is programmed to recognize and temporarily record in memory the largest output current signal from the sensor as a zero baseline reference (clean air). The microprocessor then sends a signal to the output indicator to indicate a zero reference (null) signal. If the instrument was first turned on in an area where there was background contamination, the value recorded in memory as a baseline reference will not be as high as it would be for clean air. Thereafter, the microprocessor reads the output of the analog to digital converter every 30 milliseconds and as the output of the sensor increases, the microprocessor is programmed to replace the previously recorded sensor output signal with the larger sensor output signal which in practice corresponds to less contamination (cleaner air). The microprocessor is programmed to establish the zero baseline reference as close to olean air conditions as possible. It is not programmed to "tune out" or bias out variations in the ambient due to the presence of small amounts of halogens.

After approximately three seconds have elapsed during which the microprocessor has read the output of the analog to digital converter approximately 60 times and replaced the recorded (baseline reference) high, whenever there was a greater high, the microprocessor is programmed to replace the baseline reference with the next output from the analog to digital converter, whether it is higher or lower than the baseline reference, and then continue as before making measurements every 30 milliseconds and replacing the baseline reference signal whenever the signal increases. This portion of the program is designed to compensate for the aging of the sensor element as well as slow-drift characteristics induced by variations in temperature, humidity, etc.

The microprocessor is programmed to calculate the output changes of the analog to digital converter as percentage changes of full scale. In the corona discharge detector described herein, a one percent change (decrease) in corona current represents approximately a 30 ppm concentration of freon 12 in clean air and is programmed to be the threshold of response of the output indicator in the normal mode of operation. Lower threshold levels are possible depending on the noise output of the sensor. If a one percent or greater change (decrease) in corona current occurs, the microprocessor suspends both modes of baseline update and signals an output indicator proportional to the percentage change in the sensor current. Both modes of baseline update continue to be suspended until the measured corona current returns to less than the one percent threshold value. If a 10 percent change in sensor corona current occurs, the baseline update program is suspended as before and an output proportional to the concentration of freon is indicated. In the detector described herein, there are two selectible output indications given. An audible alarm indication consisting of a speaker with associated components and a visual indication consisting of a 10 segment LED bar graph display calibrated in 10 percent increments to indicate 10 percent changes in the sensor corona current from zero percent to 100 percent.

By calculating the percentage change of the sensor output current and providing an output proportional to it instead of by measuring the absolute change in sensor output current, the variation in the sensitivity of the corona discharge sensors is for all practical purposes eliminated.

The method described in the present invention is not only applicable to refrigerant leak detection, another practical application for this method can be found in the field of temperature measurement with thermistors.

Thermistors are semiconductor devices which have a large negative temperature coefficient of resistance. They are widely used in temperature measurement and control applications in the range of −50° C. to +150° C. because of their ruggedness, ease of use and relatively low cost.

The traditional way of measuring temperature with a thermistor is to determine the resistance of the device and to convert that resistance to a temperature value using a number of standard circuits or, in a microprocessor based application, by solving the Steinhart-Hart equation which relates the resistance of the thermistor to its temperature or by looking up the temperature in a resistance vs. temperature table stored in a ROM. The disadvantage of this approach is that it requires thermistors that are matched to a certain accuracy with respect, not just to the resistance vs. temperature relationship, but also with respect to their absolute resistance value. This renders the parts more difficult to manufacture and, consequently, more expensive.

By taking advantage of the method described in this patent, one could use a thermistor parameter called BETA or material constant to measure temperature. This parameter defines the percentage change in resistance with temperature for a given thermistor material. Since it is a property of the material formulation of the thermistor and not of the thermistor itself, the BETA is more reproducible than the absolute resistance vs. temperature relationship and so the part is easier to fabricate and, thus, cheaper.

To implement the method described in the present invention in the context of thermistor temperature measurements, one would start by measuring the resistance of the part at a known temperature, say, 25° C., and, using this value as a baseline, take subsequent resistance measurements, compute the percentage change from the known baseline resistance and then, using the BETA, determine the current temperature of the thermistor.

DESCRIPTION OF THE PREFERRED EMBODIMENT

Figure 1:
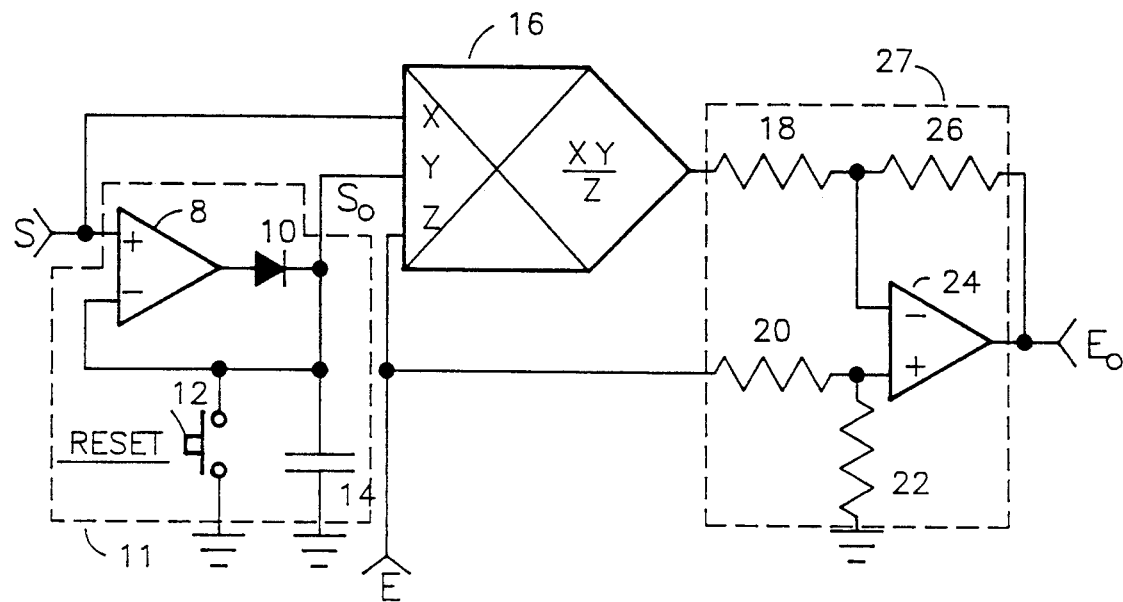
FIG. 1 is an electronic schematic drawing of an analog embodiment of the present invention.

An analog schematic is shown in FIG. 1. However, the schematic shown in FIG. 1 is not a preferred implementation of the present invention due to the careful attention that needs to be given to calibration, offsets, etc. in the analog multiplier/divider. The schematic shown in FIG. 1 will be used to illustrate the computations involved for determing the percentage change.

In accordance with FIG. 1, let the value of a sensor output at some predetermined instant in time be So. If, at a later time, the output of the sensor has a value S, the percent change of the sensor output, with respect to So, is:

$$\% \text{ change} = 100*[(S_o - S)/S_o]$$

or $$\% \text{ change} = 100 - [(100*S)/S_o] \quad (1)$$

As seen in FIG. 1, amplifier 8, diode 10, capacitor 14 and RESET switch 12 form a resettable peak detector 11. As long as the RESET switch 12 is open, the voltage So across capacitor 14 will be the maximum value of the input voltage S since amplifier 8 will drive diode 10 to conduct any time that S exceeds So. Further more, as long as RESET switch 12 is closed, So will be made equal to zero; as soon as switch 12 is opened, So will become equal to the value of S at the moment switch 12 was opened. In this manner, RESET switch 12 controls the initial value of So While amplifier 8, and diode 10 ensure that So will always equal the highest value of S from the last time switch 12 was opened.

Multiplier/divider 16 does most of the percent calculations. Although most multipliers in the market are of the (X*Y)/10 kind, vendors such as Analog Devices market (X*Y)/Z full function devices. The output of multiplier/divider 16 is $$(E*S)/So$$

and, therefore, there exists the possibility of the output of the multiplier/divider 16 going to saturation, especially when the RESET switch 12 is closed and So equal zero.

Finally, amplifier 24 and resistors 18, 20, 22 and 26, all of EQUAL value, form a unity gain differential amplifier 27.

The output of amplifier 24 is Eo and can be written as:

$$Eo = E - [(E*S)/So] \qquad (2)$$

If E is allowed to equal (k×100) and is substituted in equation 2, it follows that $$Eo = k[100 - ]100 \times S)/So]] \qquad (3)$$

this indicates that the output of amplifier 24 is a constant k times the percent change in S with respect to So.

RESET switch 12 can be used to automatically compensate for drift in the input signal S. For example, switch 12 can be periodically closed every three seconds or so to obtain a new baseline value for the calculations provided that the output of amplifier 24 is zero or some small percentage used as an alarm threshold.

Practical implementation of the objectives presented in the present invention requires the performance of computations on the magnitude of the sensor output.

Since these computations go beyond the more common scaling (multiplication) and offsetting (adding and subtracting) operations, the preferred embodiment of this method requires a digital program implemented in a microcomputer as well as an analog to digital converter to reduce the analog sensor output to a form suitable for digital processing.

Figure 2:
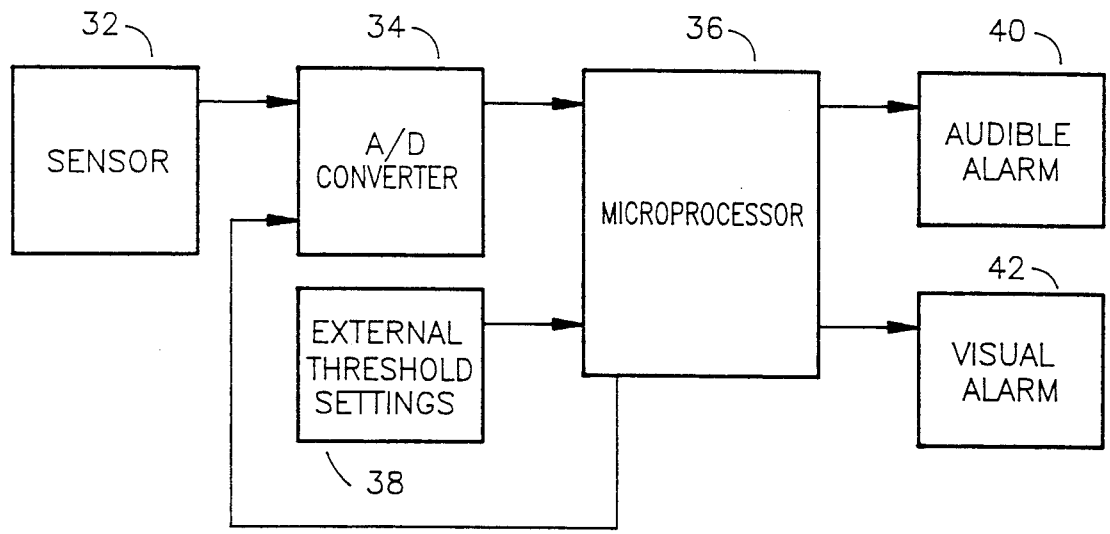
FIG. 2 is a block diagram of the preferred embodiment.
Figure 4:
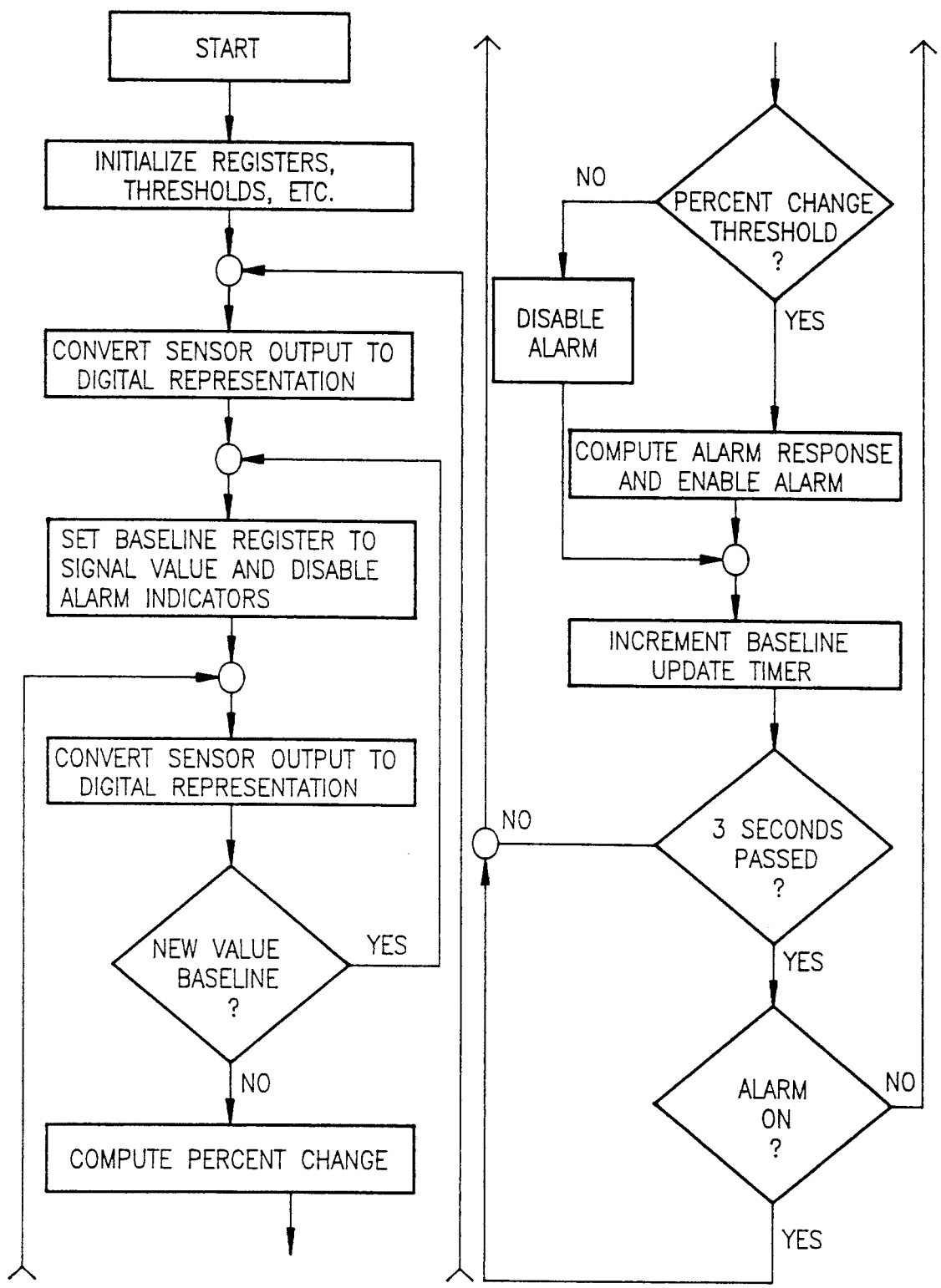
FIG. 4 is a flow chart of the program used in conjunction with the preferred embodiment.

The preferred embodiment of the invention is schematically shown in FIG. 2 with the general flow chart of the algorithm shown in FIG. 4.

When power is first applied to the circuit of FIG. 2, the microprocessor 3 is reset and starts executing the stored program. The first few steps in the program initialize various internal registers, reads the external threshold settings 38 and disables the various alarms 40 and 42.

Next, microprocessor 36 requests analog to digital converter 34 to take a reading of the output of sensor 32. This reading is temporarily recorded in an internal register of microprocessor 36 and used as a baseline reference for the percent change calculations.

This initial reading is not permanently set in microprocessor 36's internal registers. Rather, the value of the baseline is a dynamically allocated quantity which can be changed, and is in fact changed, depending on several conditions as will be shown below After the initial value of the baseline is recorded in a machine register of microprocessor 36, subsequent readings of sensor 32's output by the analog to digital converter 34 are evaluated and one of the following actions is taken:

(1) If the magnitude of the present reading is higher than the currently recorded baseline, the present reading replaces the recorded baseline in the internal register of microprocessor 36.

(2) If the present reading is lower in magnitude than the presently recorded baseline, a computation of the percent change is carried out digitally by microprocessor 36 and the result is used to activate any one of several alarm indicators.

Since the main loop of the program in microprocessor 36 is very regular, it can be concurrently used as a software timing loop. In this manner, counting a large number of passes through this loop can be used to establish a time delay for the automatic re-evaluation of the baseline. In the preferred embodiment, sufficient passes through the main loop are counted to account for about three seconds, at which time and, provided that none of the alarm indicators is on, the next reading of analog to digital converter 34 is automatically recorded as the baseline reference. This adaptive technique used for establishing the baseline accounts for the present invention's ability to compensate for slow drifts in the sensor 32's output.

Once the percent change calculation has been carried out and a value obtained, this value is compared to a threshold which was either obtained during the initialization process by reading the setting of external threshold setting 38 o is obtained by reading the threshold setting 38 once ever execution of the main loop so the user can change the thresholds at will during the execution of the program. Whenever the calculated percent exceeds the threshold, an alarm indicator is activated by microprocessor 36.

Many different kinds of alarm indicators are possible and more than one can be active at any one time. In a preferred embodiment, an audible alarm indicator is implemented using a pair of timers internal to the microprocessor to generate a variable frequency pulse train. The frequency is made proportional to the percent change and the pulse train is used to drive a speaker so that a variable frequency tone alerts the user to the relative magnitude of the output from sensor 32.

Another alarm indicator consists of a bank of light emitting diodes which are turned on so that the total number of diodes lit or the position of the diode being lit corresponds to a known percent change in the sensor output.

At this point, the main loop repeats itself by requesting a new reading of the sensor output from the analog to digital converter 34.

All of the preceeding discussion has been implicitly carried out in the context of negative percent changes, that is, the sensor output value taken as the baseline is assumed to be the highest or full scale value of said output and all subsequent measurements are either lower in magnitude or used as the new baseline. Although this is certainly the most often used and most practical contest, there are no fundamental limitations in the present invention which would prevent it from computing and using both positive and negative percent changes. By modifying equation 1 to read $$\% \ change = 100[(S/So) - 1] \qquad (4)$$

it is seen that for S<So, negative percent changes are obtained and for S>So positive percent changes are obtained.

Such "bipolar" percent change calculations may be useful in the case of, say, a resistive temperature sensor where the percent change in resistance is proportional to temperature. In such a case, the baseline would be the resistance at some reference temperature and then both negative as well as positive percent changes could be calculated to measure temperatures above and below the reference.

Figure 3:
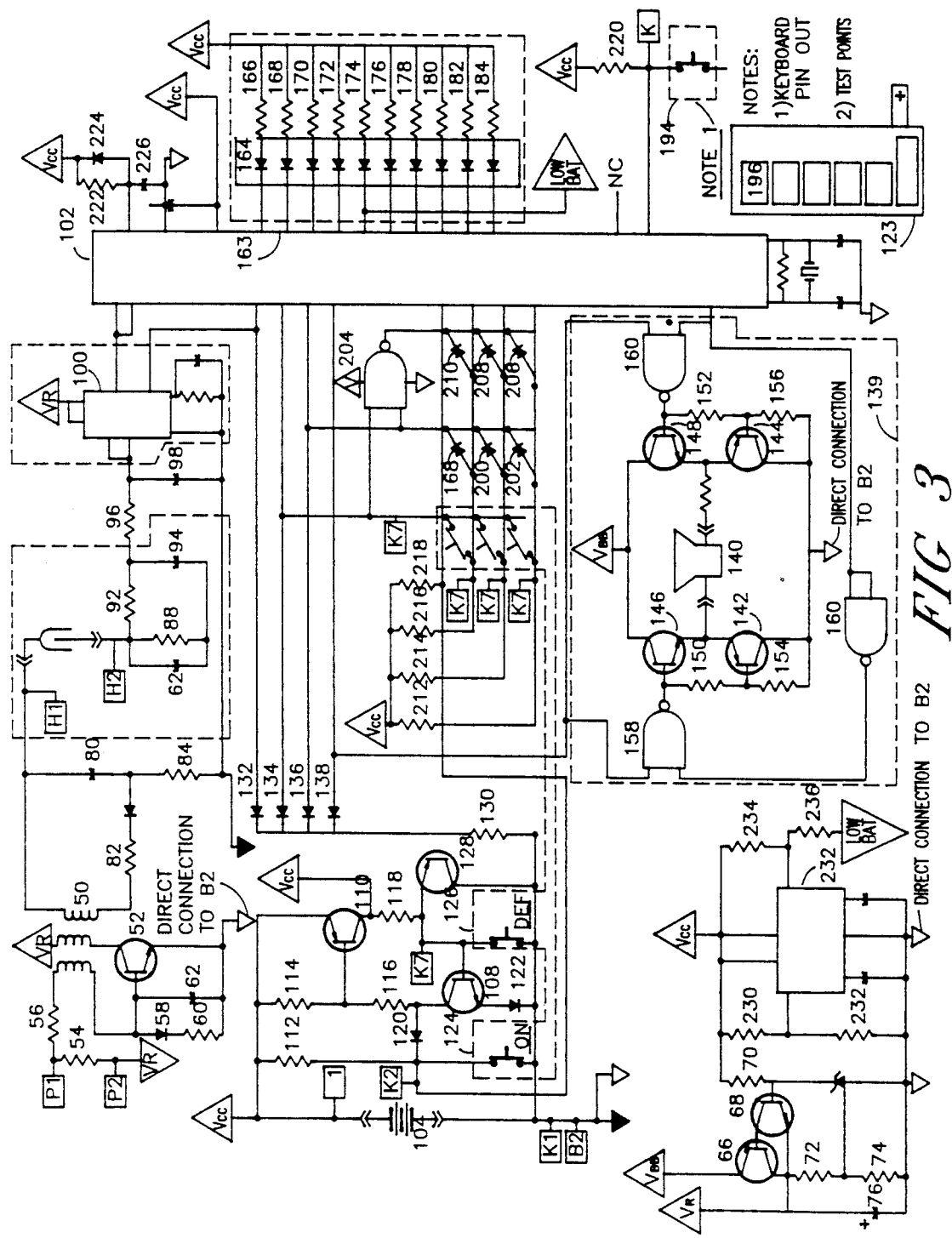
FIG. 3 is an electronic schematic drawing of the preferred embodiment.

Referring now to FIG. 3, the details of the electronic schematic of the invention will be described. A blocking oscillator circuit 49 consisting of transformer 50, transistor 52, resistors 54, 56 and 60, compacitor 62 and diode 58, produces high voltage pulses across terminals 1 and 2 of transformer 50. The magnitude of the voltage pulses is adjusted by selecting the value of resistor 54 during production. The blocking oscillator circuit is powered by a regulated voltage supplied by active reference 64, transistors 66 and 68, resistors 70, 72 and 74 and capacitor 76. Preferably, the magnitude of this voltage is set by design to be approximately four volts DC.

The high voltage pulses across terminals 1 and 2 are rectified and filtered by diode 78 and capacitor 80 to produce a positive DC voltage having a value of approximately 2,300 volts across terminals H1 and with no tip connected. Resistors 82 and 84 are included to limit the discharge current in case of arcing.

The 2300 volts DC is applied across an asymmetrical electrode pair 86 in series with resistor 88. The potential difference established produces a continuous electric discharge which is very sensitive to the presence of halogenated gases. A voltage is developed across resistor 88 which is proportional to the magnitude of the discharge current and, therefore, proportional to the level of halogen gas in the vicinity of the discharge. This voltage is filtered by capacitors 90, resistor 92 and capacitor 94.

Resistor 96 and capacitor 98 provide the RC time constant elements for monostable multi-vibrator 100. Whenever the software running in microprocessor 102 needs to obtain a reading of the corona current, it toggles pin 22 of microprocessor 102 and initiates a cycle of the monostable 100. The output of monostable 100 is a pulse which goes to a high level whenever a trigger pulse is sent by microprocessor 102 and stays at a high level for a time directly proportional to the value of the voltage drop across resistor 88. This output pulse gates a 16 bit counter internal to microprocessor 102, a number of microprocessor clock cycles is accumulated in the counter which is proportional to the width of the pulse from multivibrator 100 and, therefore, to the discharge current in the sensor.

The six-volt DC supply from the batteries 106 is switched to the circuit by a bi-stable latch comprised of transistors 108 and 110 and resistors 112, 114, 116 and 118, diodes 120 and 122 as well as the momentary key pad contacts 123 at terminals 1, 2 and 7. Whenever the "ON" key 124 in key pad 123 is depressed, transistor 110 is made to conduct which, in turn, sends current through the base of transistor 108 turning it on and making it act as if "ON" key 124 was permanently depressed. The "OFF" contact 126 of key pad 123 shorts off the base of transistor 108 making transistor 110 stop conducting and shutting off the power to circuit 48.

Transistor 128, resistor 130 and diodes 132, 134, 136 and 138 make up a discrete AND gate 131 which is activated by microprocessor 102 to shut off the power to circuit 48. AND gate 131 is needed because all of the available lines are used for other purposes at various stages in the operation of the software, therefore, it is necessary to combine the lines to achieve this automatic shut-off.

Two types of alarm indications are provided to the user to signal the presence as well as the relative amount of halogen gas. The first type is an audible alarm 139 which consists of a variable frequency, variable duty cycle pulse train modulating a variable frequency tone. The second type is a visual display 163 which consists of 10 LED'S in a row, each one indicating a different level of halogen gas concentration. Either one or both 12 alarm types can be selected from key pad 123.

The software running in microprocessor 102 utilizes hardware internal to microprocessor 102 to generate both the modulating pulse and the modulated tone. Speaker 140 in the unit is driven by an "H" driver consisting of transistors 142, 144, 146 and 148 with associated bias resistors 150, 152, 154, and 156. The purpose of this driver is to be able to power speaker 140 with a peak to peak signal amplitude of twice the magnitude of the instrument supply voltage to obtain four times the power of the more conventional single ended driver.

A balance modulator is needed to drive the "H" driver. This modulator is made up of three NAND gates 158, 160, and 162. The variable frequency tone is source from pin 15 of microprocessor 102 and drives one input to NAND gates 158, 160 and 162, the other input is source from pin 19 of microprocessor 102 and is a variable frequency, variable duty cycle pulse train.

The visual indicator is made up of ten LEDs connected to the microprocessor's 102 I/O lines and to current limiting resistors 166, 168, 170, 172, 174, 176, 180, 182 and 184. The software running in microprocessor 102 directly turns on the appropriate LED through the I/O lines.

The user interacts with the software by way of key pad 123. The ALARM SELECT and HIGH keys 188 and 192 are enabled by bringing down pin 21 of microprocessor 102 and determining which of input pins 8, 9 or 10 is low. The CLEAR key 194 is a direct input to microprocessor 102 as is the NORMAL key 196. The software simply reads those pins to determine the state of the corresponding key. The "OFF" key 126 is a direct connection to the base of transistor 108 as explained above.

Pin 20 of microprocessor 102 is brought low once at the cold start of the software to determine the status of external jumpers diode 198, 200 and 202. The presence or absence of these diode jumpers is interpreted by the software as one of the eight possible threshold values for the normal gain mode of operation. These values determine at what percentage change in the corona discharge current, the instrument starts to sound the alarm.

Pins 20 and 21 of microprocessor 102 are simultaneously brought high while keeping pins 19 and 22 low to cause NAND gate 204 to bring its output low. This is also done once at the cold start of the software to determine the status of jumper diodes 206, 208 and 210. The presence or absence of these diode jumpers determine the threshold of operation in the high gain mode of operation.

Resistors 212, 214, 216, 218 and 220 are used as pull-ups for the corresponding input lines, this insures that these are normally at a high level.

Resistor 222, diode 224 and capacitor 226 make up the power on reset circuit for microprocessor 102.

Chip 228 is a voltage supervisor IC which is used, in conjunction with resistors 230 and 232, to signal the presence of a low battery condition. Pull up resistor 234 and current limiting resistor 236 are used to light the fifth LED in the string of 10 LEDs at half brightness to signal the user it is time to change battery 104. The values of resistors 230 and 232 determine the battery voltage at which a low battery condition exists. Preferably, a low battery condition will exist at 4.5 volts DC.

In operation, the software alternates among one of the three possible functions:

(1) Determining the percentage change in the corona discharge current flowing in the sensor. This involves determining a baseline value for the current by taking an initial reading through multivibrator 100 and subsequently computing percentage changes from that baseline value. If, at any time, the present value of the sensor current is higher than the current baseline, the higher value is taken as a new baseline. Preferably, a reading of the corona current is taken approximately every 25 milliseconds.

(2) Activating the audible or the visual alarm or both. The audible alarm sounds at a frequency and duty cycle proportional to the percentage change in the sensor current. Preferably, the range is from 40 to 4,000 hertz and there are approximately 100 different tones in that range. In the normal mode of operation, the entire alarm range is evenly distributed over a 0 to 100 percent current change whereas in the high gain mode, the entire alarm range is used over a 0 to 12.5 percent current change. The visual alarm lights up one of 10 red LEDs dependent on the percentage change computed. In the normal mode of operation, each LED corresponds to approximately 10 percent change while in the high gain mode, each LED is approximately 1.2 percent. Either alarm is activated whenever the percentage change calculated exceeds an externally set threshold.

(3) Scan the key pad to determine which mode the user is requesting. Preferably, two modes will be utilized, HIGH and NORMAL. However, any number of modes can be utilized, each having its own threshold value, by adding additional circuitry to circuit 48. The CLEAR key 194 is significant in that it resets the baseline used for the percentage calculations regardless of the mode currently in use.

Lastly, a flow chart of the program implemented within microprocessor 36 of FIG. 2 or microprocessor 102 of FIG. 3 is shown in FIG. 4.

The instant invention has been shown and described in what is considered to be the most practical and preferred embodiment. While there has been described above the principles of this invention in connection with the specific apparatus, it is to be clearly understood that this description is made only by way of example and not as a limitation to the scope of the invention. It is recognized that departures may be made therefrom within the scope of the invention and that obvious modifications will occur to a person skilled in the art.

What I claim is:

1. A method for automatically measuring a change in a sensor's output, in terms of percentage, for pinpointing gas leaks comprising the steps of:
   (a) supplying power to a circuit;
   (b) initializing various internal registers of a microprocessor;
   (c) reading an external threshold setting;
   (d) reading a sensor's output;
   (e) converting said sensor's output to a digital representation by an analog to digital converter;
   (f) temporarily recording said digital representation in one of said various internal registers of said microprocessor for use as a baseline reference and disabling an alarm;
   (g) reading and converting a next sensor's output to a next digital representation by said analog to digital converter;
   (h) determining if said next digital representation is greater than said baseline reference;
   (i) replacing said baseline reference with said next digital representation as the new baseline reference and returning to step (g) if said next digital representation was greater than said baseline reference;
   (j) computing said percentage change between said next digital representation and said baseline reference if said next digital representation was less than said baseline reference;
   (k) determining if said percent change is greater than said threshold setting;
   (l) computing an alarm response and enabling said alarm if said percentage change is greater than said threshold setting;
   (m) incrementing a baseline update timer;
   (n) determining from said timer if a time period has been reached;
   (o) returning to step (g) if said time period has not been reached;
   (p) determining if said alarm is enabled if said time period has been reached;
   (q) returning to step (g) if said alarm is enabled; and
   (r) returning to step (d) if said alarm is not enabled.

2. The method of claim 1, wherein said time period is 3 seconds.

3. An apparatus for automatically measuring a change in a sensor's output, in terms of percentage, for pinpointing gas leaks, the sensor operating at a constant high voltage level and the apparatus having a continuous output indication proportional to the percentage, comprising:
   (a) means for providing a plurality of analog outputs from the sensor;
   (b) means for converting said analog outputs to a plurality of digital representations, said digital representations have a value;
   (c) means for temporarily storing a first of said plurality of digital representations as a baseline reference;
   (d) means for comparing said digital representations to said first digital representation;
   (e) means for continuous replacement of said baseline reference to reflect a greatest digital representation value;
   (f) means for computing a percentage change of the value difference when said digital representation is less than said greatest digital representation value;
   (g) means for providing a threshold value for comparison with said percentage change;
   (h) means for indicating when said percentage change is greater than said threshold value; and
   (i) mean for resetting said apparatus without operator assistance.

4. The apparatus of claim 3, wherein said means for providing a plurality of analog outputs is a current discharge sensor.

5. The apparatus of claim 3, wherein said means for converting is an analog to digital converter.

6. The apparatus of claim 3, wherein said means for temporarily storing is a random access memory located within a microprocessor.

7. The apparatus of claim 3, wherein said means for comparing, said means for continuous replacement and said means for computing is a program implemented within said microprocessor.

8. The apparatus of claim 3, wherein said means for indicating is a visual display.

9. The apparatus of claim 8, wherein said visual display is an LED display.

10. The apparatus of claim 3, wherein said means for indicating is an audible display.

11. The apparatus of claim 10, wherein said audible display is a speaker with associated drive components.

12. The apparatus of claim 3, wherein said means for resetting is a counter/timer located within said microprocessor.

13. An apparatus for automatically measuring a change in a sensor's output, in terms of percentage, for pinpointing gas leaks, the sensor operating at a constant high voltage level and the apparatus having a continuous output indication proportional to the percentage, comprising:
   (a) means for supplying power to a circuit;
   (b) means for initializing various internal registers of a microprocessor;
   (c) means for reading an external threshold setting;
   (d) means for reading a sensor's output;
   (e) means for converting said sensor's output to a digital representation;
   (f) means for temporarily recording said digital representation in one of said various internal registers of said microprocessor for use as a baseline reference and disabling an alarm;
   (g) means for reading and converting a next sensor's output to a next digital representation by said means for converting;
   (h) means for determining if said next digital representation is greater than said baseline reference;
   (i) means for replacing said baseline reference with said next digital representation as a new baseline reference and reading a next sensor's output from said means for reading and converting if said next digital representation was greater than said baseline reference;
   (j) means for computing a percentage change between said next digital representation and said baseline reference if said next digital representation was less than said baseline reference;
   (k) means for determining if said percentage change is greater than said threshold setting; and
   (l) means for computing an alarm response and enabling said alarm if said percentage change is greater than said threshold setting.

14. The apparatus of claim 13, further including
   (a) means for incrementing a baseline update timer;
   (b) means for determining from said timer if a time period has been reached;
   (c) means for reading and converting a next sensor's output to a next digital representation if said time period has not been reached;
   (d) means for determining if said alarm has been enabled if said time period has been reached and reading and converting a next sensor's output to a next digital representation if said alarm has been enabled; and
   (e) means for reading a sensor's output if said alarm is not enabled.

* * * * *